United States Patent [19]

Touge et al.

[11] Patent Number: 5,180,065
[45] Date of Patent: Jan. 19, 1993

[54] APPARATUS FOR AND METHOD OF FRACTIONATING PARTICLE IN PARTICLE-SUSPENDED LIQUID IN CONFORMITY WITH THE PROPERTIES THEREOF

[75] Inventors: Yoshiyuki Touge; Yoshito Yoneyama, both of Kawasaki, Japan

[73] Assignee: Canon Kabushiki Kaisha, Tokyo, Japan

[21] Appl. No.: 596,083

[22] Filed: Oct. 11, 1990

[30] Foreign Application Priority Data

Oct. 11, 1989 [JP] Japan ............................. 1-264553
Aug. 30, 1990 [JP] Japan ............................. 2-229679

[51] Int. Cl.$^5$ ................................. B07B 5/36
[52] U.S. Cl. ................................. 209/577; 209/639; 209/644; 209/906; 209/3.1; 222/420
[58] Field of Search ............... 209/3.1, 576–577, 209/579, 639, 644, 906, 587; 222/420; 356/39; 417/52; 346/75

[56] References Cited

U.S. PATENT DOCUMENTS

| | | | |
|---|---|---|---|
| 3,380,584 | 4/1968 | Fulwyler | 209/3 |
| 3,550,771 | 12/1970 | Spyropoulos | 209/906 X |
| 3,710,933 | 1/1973 | Fulwyler et al. | 209/3 |
| 3,741,726 | 1/1973 | Mitchell et al. | 23/230 R |
| 3,747,120 | 7/1973 | Stemme | 346/75 |
| 3,826,364 | 7/1974 | Bonner et al. | 209/3 |
| 4,279,345 | 7/1981 | Allred | 209/3.2 |
| 4,341,310 | 7/1982 | Sangiovanni et al. | 209/638 |
| 4,361,400 | 11/1982 | Gray et al. | 209/906 X |
| 4,492,322 | 1/1985 | Hieftje | 209/644 X |
| 4,526,276 | 7/1985 | Shoor et al. | 209/552 |
| 4,723,129 | 2/1988 | Endo et al. | 417/52 X |
| 4,866,283 | 9/1989 | Hill, Jr. | 209/579 X |

FOREIGN PATENT DOCUMENTS

| | | |
|---|---|---|
| 2920371 | 12/1979 | Fed. Rep. of Germany . |
| 3126854 | 1/1983 | Fed. Rep. of Germany . |
| 57-211557 | 12/1982 | Japan . |

OTHER PUBLICATIONS

Proceedings of the IEEE, vol. 57, No. 11, N.Y., U.S. pp. 2007–2016 L. Kamentsky et al. "Instrumentation for automated examinations of cellular specimens."
L. Winnar, SID International Symposium 1983, May 1, 1983, Coral Gables, Fla.

Primary Examiner—Donald T. Hajec
Attorney, Agent, or Firm—Fitzpatrick, Cella, Harper & Scinto

[57] ABSTRACT

This invention measures the properties of individual particles in particle-suspended liquid by an optical technique or the like, causes the particle-suspended liquid to fall while separating the liquid into droplets containing the individual particles therein, and causes liquid droplets discharged from a nozzle to collide with the droplets from a direction differing from the direction of fall, in conformity with the properties of the particles discriminated by the measurement, so as to change the direction of fall of the falling droplets, thereby fractionating the particles.

16 Claims, 7 Drawing Sheets

APPARATUS FOR AND METHOD OF FRACTIONATING PARTICLE IN PARTICLE-SUSPENDED LIQUID IN CONFORMITY WITH THE PROPERTIES THEREOF

BACKGROUND OF THE INVENTION

1. Field of the Invention

This invention relates to an apparatus for and a method of measuring the properties of individual particles in particle-suspended liquid and fractionating the particles on the basis of the result of the measurement.

2. Related Background Art

As an example of the apparatus of this kind, an apparatus as shown in FIG. 6 of the accompanying drawings has been put into practical use under the name of cell sorter. The basic principles of the cell sorter are also disclosed in U.S. Pat. Nos. 3,380,584, 3,710,933, 3,741,726, 3,826,364, etc.

In FIG. 6, sample liquid such as blood which is cell-suspended liquid and sheath liquid such as physiological salin solution are stored in a sample container 1 and a sheath container 2, respectively, and are pressurized by a compressor or a nitrogen gas cylinder and a regulator or the like and directed to a nozzle 5, from which the sample liquid and sheath liquid are injected as a fine stream 6 into the atmosphere. Consequently, by virtue of the sheath flow principle, the sample liquid is wrapped up in the sheath liquid and forms a fine stream in the sheath liquid and thus, the cells in the sample liquid flow one by one. By the vibration of a vibrator 7 mounted on the nozzle 5, the fine stream 6 later falls as droplets 8. A laser beam from a laser source 9 is applied to the intermediate portion of the fine stream 6, whereby the intensity of scattered light and the intensity of fluorescence emitted from the cells in the fine stream are metered by photodetectors 14 and 17, respectively. From the resulting measurement, the properties of the cells are analyzed on real time and in conformity with the result thereof, a charging voltage of positive or negative or 0 is applied to the fluid by charging means, not shown, whereby the droplets 8 are charged to positive or negative or 0. High voltage electrostatic deflecting plates 26a and 26b and disposed in opposed relationship with each other along the falling orbit of the droplets, and the falling cell droplets are deflected in directions conforming to the charges thereof and fall into different containers 27, 28 and 29. Thus, the cells can be fractionated and gathered in conformity with the properties thereof.

However, in the above-described particle fractionating apparatus according to the prior art, the cells must be charged immediately before they become droplets, and subtle regulation is required. Thus, it has been difficult to maintain a stable operation at all times.

Also, a high voltage must be handled, and this leads to a problem of involving a danger.

Further, basically, the cells can only be fractionated into three kinds of cells, i.e., cells charged to positive, cells charged to negative, and cells charged to neither. It would also appear reasonable to change the charging voltage into two strong and weak kinds and utilize the magnitude of the amount of deflection by the strength of the charging to divide the cells into five kinds, but this would lead to the problem that even if the charging can be accomplished accurately, the size, i.e. mass, of droplets will not always be constant and therefore the amount of deflection will vary and accurate fractionation cannot always be accomplished.

SUMMARY OF THE INVENTION

It is an object of the present invention to provide an apparatus and a method which can reliably accomplish the fractionation of many kinds of particles by a simple construction.

It is another object of the present invention to provide a highly safe apparatus which does not require handling a high voltage.

It is still another object of the present invention to provide an apparatus and a method which can accomplish the fractionation of particles at a high speed.

It is yet still another object of the present invention to provide a compact apparatus and a method which do not use a pressurizing mechanism.

DESCRIPTION OF THE

DESCRIPTION OF PREFERRED EMBODIMENTS

Figure 1:
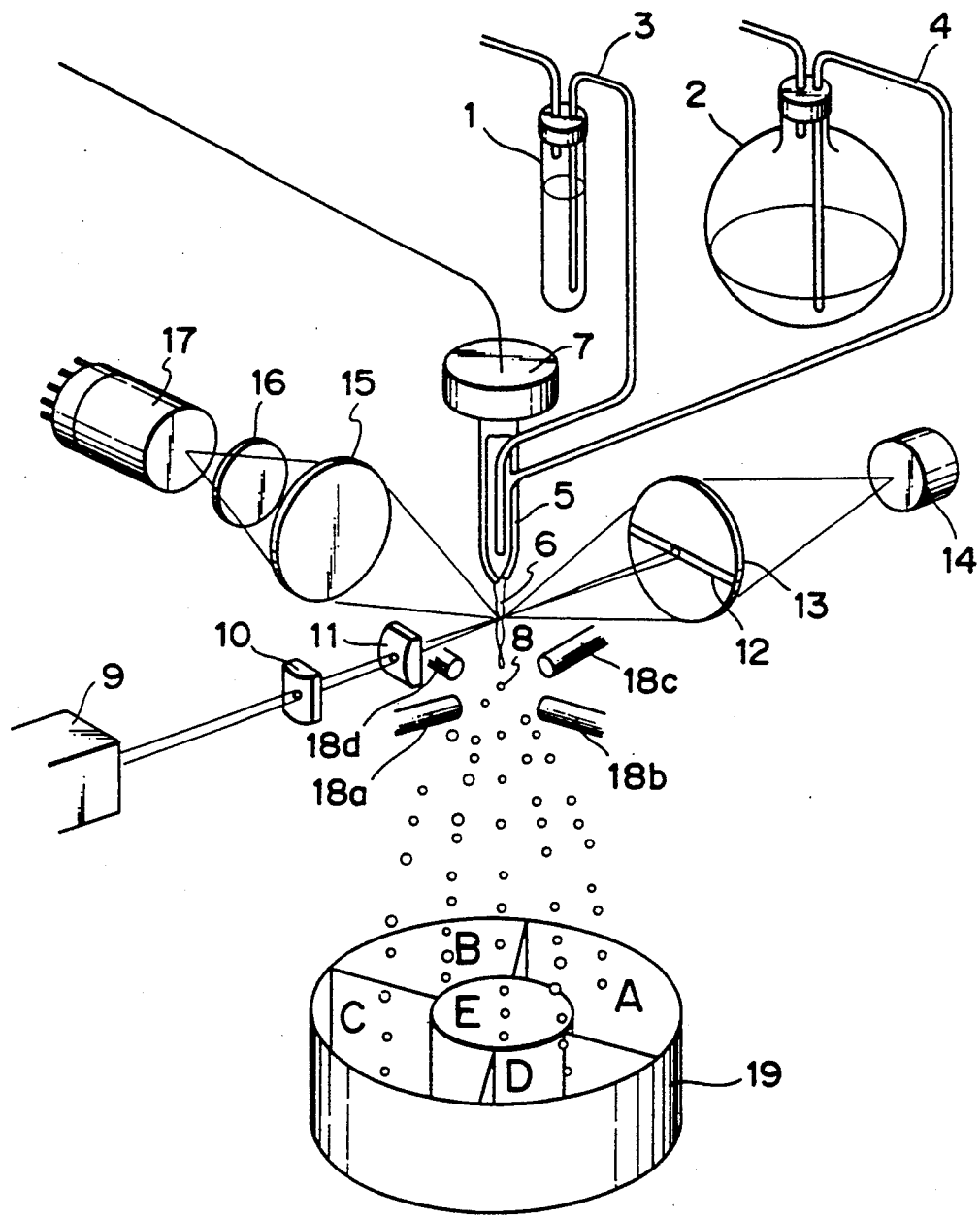
FIG. 1 shows the construction of an embodiment of the present invention.
Figure 6:
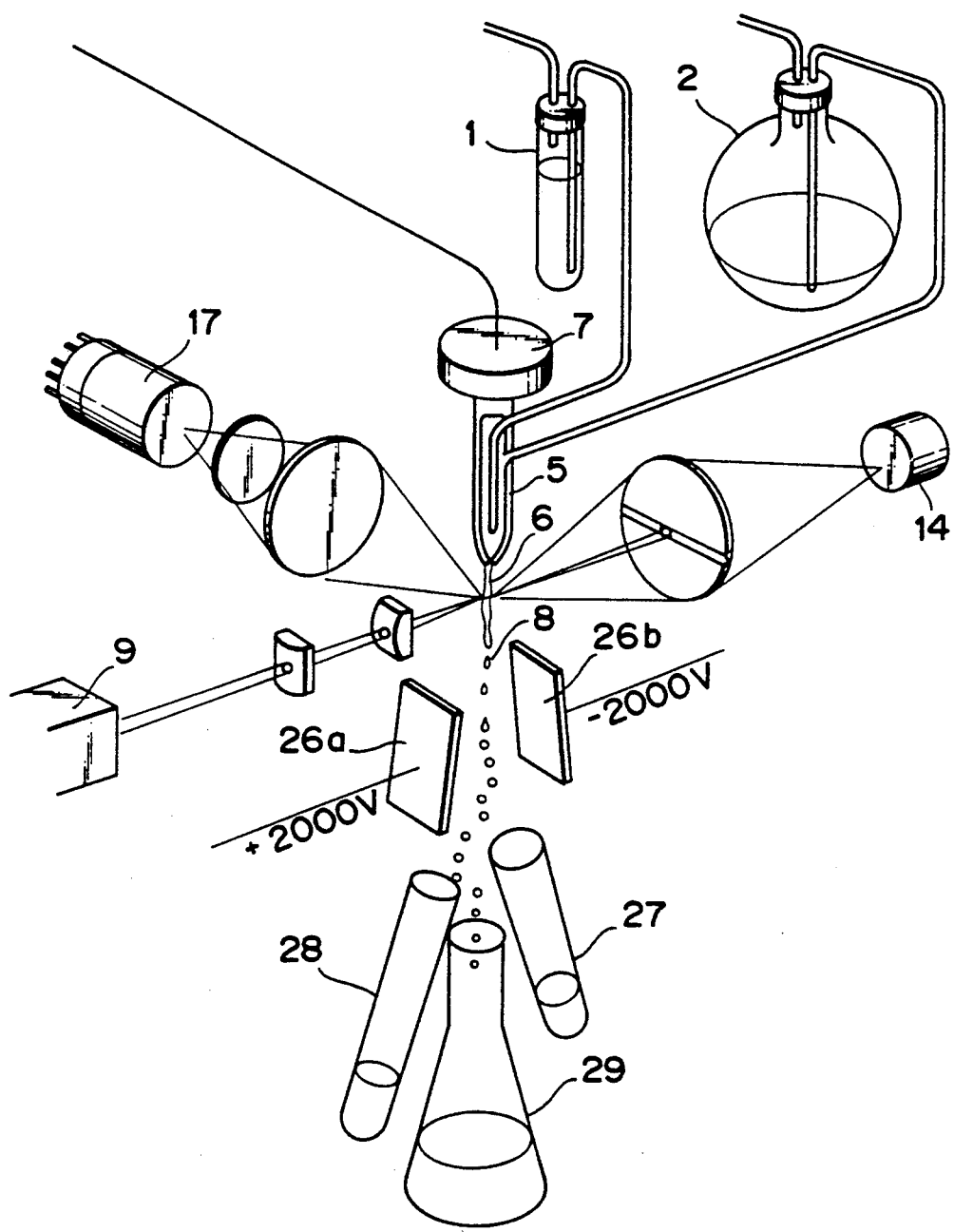
FIG. 6 shows the construction of an according to the prior art.

Embodiments of the present invention will hereinafter be described in detail with reference to the drawings. FIG. 1 is a view showing the construction of an embodiment of the present invention. In FIG. 1, the reference characters identical to those in FIG. 6 which shows an example of the prior art designate identical or similar members.

In the present embodiment, particle-suspended liquid to be fractionated is cell-suspended liquid such as blood, but the object of fractionation is not limited thereto. The present invention can also be widely used for the sorting of particles and the fractionation from dust in the field of biology, the field of industry, etc.

In FIG. 1, the reference numeral 1 designates a sample container, and the reference numeral 2 denotes a sheath container. Sample liquid which is cell-suspended liquid such as blood is stored in the sample container 1, and sheath liquid such as physiological saline solution or distilled water is stored in the sheath container 2. The sample liquid and the sheath liquid are directed to a nozzle 5 through tubes 3 and 4, respectively, and the sample liquid flows on the center axis of the interior of the nozzle 5 and the sheath liquid flows in such a manner as to wrap up the sample liquid. By virtue of the sheath flow principle, individual particles in the sample liquid pass one by one in a line. This flow is injected out as a fine stream 6 from the outlet of the nozzle 5 into the atmosphere.

A vibrator 7 is mounted on the upper portion of the nozzle 5, and the fine stream 6 is vibrated by this vibrator 7 and soon falls as droplets 8.

Discharge nozzles 18a 18d for discharging droplets are provided point-symmetrically in four directions around the course of fall of the droplets 8. Discharge ports are installed toward a fractionation point so that the liquids discharged from the discharge nozzles intersect the axis of the course of fall of the droplets of the cells at a point (hereinafter referred to as the fractionation point). Each discharge nozzle is directed somewhat downwardly toward the fractionation point, and prevents the discharged liquid from being applied to the opposed nozzle and also enhances the stability of gathering.

A circular capture container 19 is disposed below the discharge nozzles 18. The capture container 19 is divided into five compartments, and has a small circular compartment E at the center thereof, and the circular ring around it is divided into four compartments A, B, C and D. These four compartments correspond to the directions of the aforementioned four discharge nozzles 18a-18d.

A laser beam emitted from a laser source 9 is stopped into an elliptical shape by cylindrical lenses 10 and 11 and applied to the fine stream 6 in the portion to be examined. When the cells in the fine stream pass through the portion to be examined to which the light is applied, scattered light and fluorescence are emitted created from the cells. The scattered light and fluorescence are collected by light receiving lenses 13 and 15, and the intensities thereof are detected by photodetectors 14 and 17, respectively. A beam stopper 12 is provided on this side of the light receiving lens 13 so as to intercept the direct light from the laser source, and only the scattered light is detected by the photodetector 14. Also, an optical filter 16 transmitting only the fluorescence wavelength therethrough is disposed rearwardly of the light receiving lens 15, and only the fluorescence is detected by the photodetector 17.

The principle of operation of the discharge nozzles 18 will now be described with reference to FIG. 3. The diameter of each nozzle is of the order of 50 $\mu m \times 50$ $\mu m$, and in shown in FIG. 3A, the nozzle 18 is filled with liquid 22 such as physiological saline solution. The reference numeral 24 denotes a heating portion provided near the opening in the nozzle. Specifically, the heating portion is a heater in which the electrode is connected to a control circuit, not shown. The heating portion 24 is not limited to a heater, but may be means which generates heat energy, and may assume, for example, such a construction in which electromagnetic wave energy such as a laser beam is imparted to a heat absorbing member.

Figure 3A:
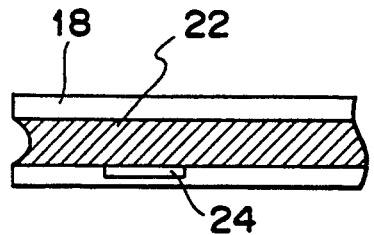
FIGS. 3A to 3E illustrate the principles of liquid droplet discharge.
Figure 3B:
Figure 3C:
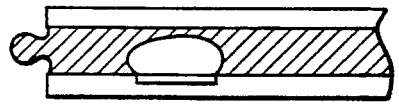
Figure 3D:
Figure 3E:
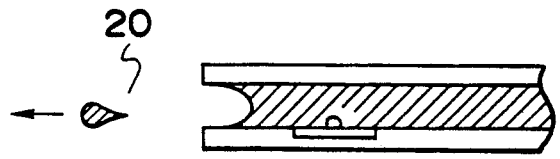

When the control circuit drives the heater 24 to heat the latter, the physiological saline solution near the heater is gasified and a bubble is created [FIG. 3B]. Thereupon, the volume increases correspondingly to the gasified amount and therefore, the physiological saline solution near the opening in the nozzle 18 is forced out of the opening [FIG. 3C].. The bubble which has continued to expand at first is cooled and begins to contract, and due to a reduction in the volume, a pull-in force acts on the physiological saline solution which has been discharged out of the opening [FIG. 3D]. The physiological saline solution which is thus discharged out of the opening flies as a droplet 20 in the air [FIG. 3E]. The physiological saline solution is supplied by a discharged amount by virtue of the capillary phenomenon and is restored to its initial state as shown in FIG. 3A. The principle of such liquid discharge utilizing heat energy is described, for example, in U. S. Pat. No. 4,723,129 and U.S. Pat. No. 4,740,796.

Figure 7A:
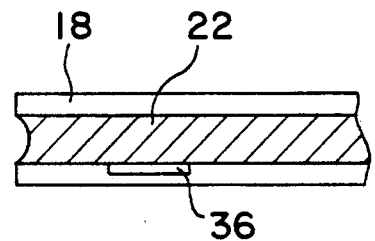
FIGS. 7A and 7B illustrate another embodiment of the principle of liquid droplet discharge.
Figure 7B:
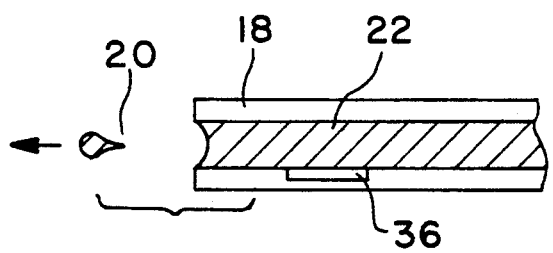

The liquid discharge system is not limited to the type as described above in which a bubble is created by heat energy to thereby discharge liquid, but liquid droplets may be discharged by the use of an on-demand type liquid droplet discharge nozzle using, for example, an electrostrictive vibrator such as a piezo-element. Accordingly, reference numeral 24 in FIG. 3A may also represent a piezo-element vibrator. FIGS. 7A and 7B illustrate the discharge of a liquid droplet using an electrorestrictive vibrator.

The operation of the apparatus of the present embodiment will now be described.

In a calculation circuit, not shown, the analysis of the properties of the cell such as the size, kind and nature of the cell is effected on real time from the detected value obtained each time a cell passes. A popular analysis method is a method of judging the size of cells in conformity with the intensity of scattered light, or a method of pre-dyeing cells with a fluorescent reagent and seeing the creation of fluorescence to thereby discriminate the nature and kind of the cells.

Control is effected by a control circuit, not shown, for a predetermined number of discharge nozzles. This is, four kinds of discharge nozzles may be driven in conformity with the conditions of desired properties such as the size, kind and nature of the cells discriminated on the basis of the result of the analysis effected on real time in the calculation circuit.

Figure 2:
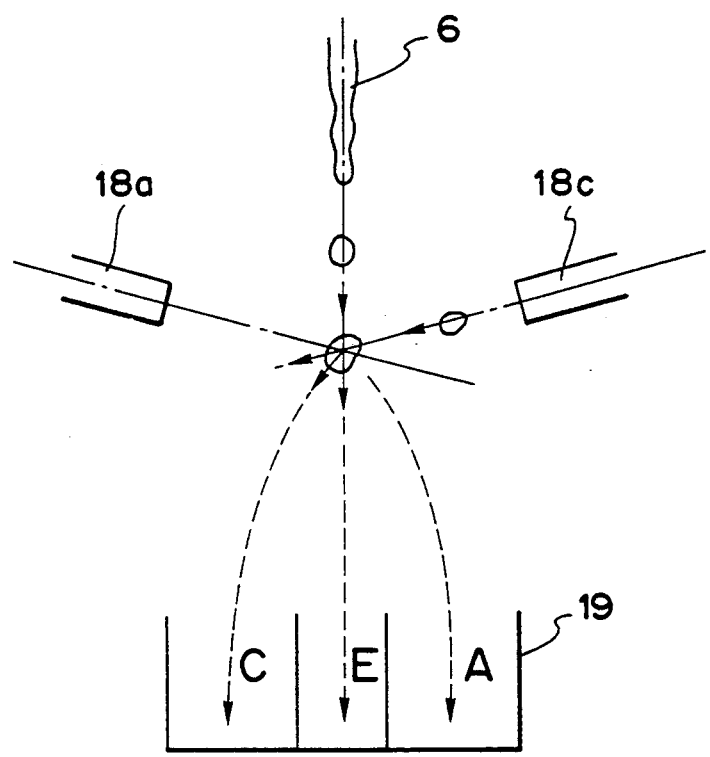
FIG. 2 illustrates the principle of fractionation.

Droplets containing therein cells, if they fall intactly, will fall into the compartment E of the capture container 19. However, if droplets of the physiological saline solution are discharged from the discharge nozzles 18, they will completely non-elastically collide with the droplets containing desired cell therein, as shown in FIG. 2, and will change the direction in which the cell droplets fall. Thus, the droplets will not fall into and be gathered in will fall into compartment E, but the compartment C of the capture container 19. If at this time, there is irregularity in the mass of the cell droplets, the fall position will more or less deviate to left or right in the plane of the drawing sheet. However since the compartments A, B, C and D of the capture container are wide in area, the droplets will be reliably fractionated. Thus, the droplets can be fractionated and gathered into five kinds A–E in conformity with the properties of the cells.

The time from a point of time at which a cell flowing in the fine stream has passed the portion to be examined, i.e, a point of time at which scattered light or fluorescence has been created and detected until a droplet containing that cell therein arrives at the fractionation point is considered to be a constant predetermined time $T_1$ if the flow velocity of the fine stream is stable. Consequently, a constant predetermined time $T_3(=T_1-T_2)$ obtained by subtracting from said $T_1$ the time $T_2$. The time after the discharge nozzles are driven until the discharged liquid arrives at the fractionation point is memorized so that the discharge nozzles may be driven when the time $T_3$ has elapsed after the light is detected. Thus, the discharged liquid can be made to accurately hit the aimed at droplet containing therein the cell.

Figure 4:
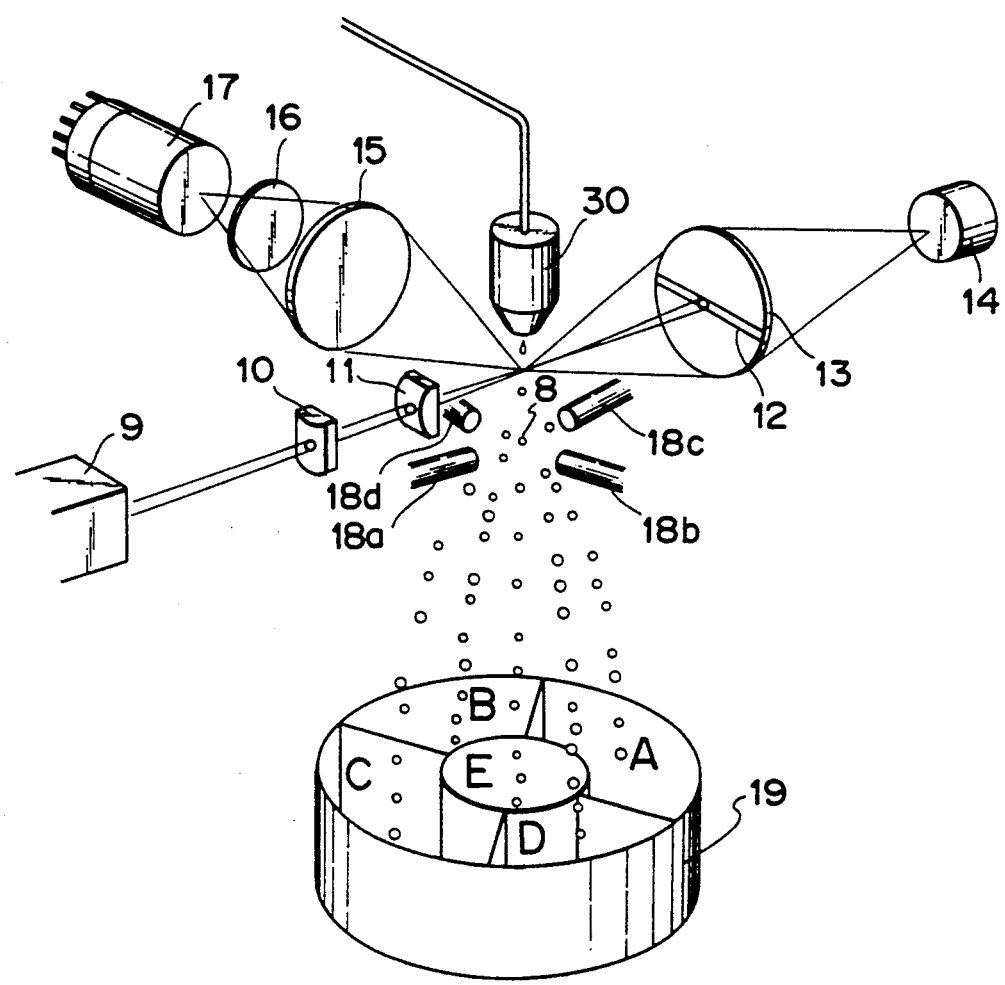
FIG. 4 shows the construction of another embodiment of the present invention.
Figure 5A:
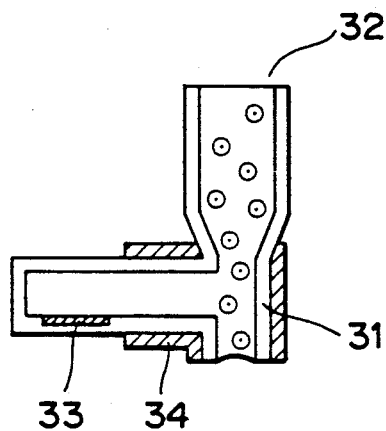
FIGS. 5A to 5D illustrate the principles of suspended liquid discharge in another embodiment.
Figure 5B:
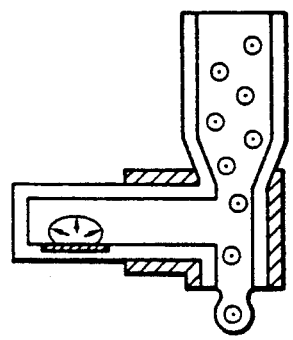
Figure 5C:
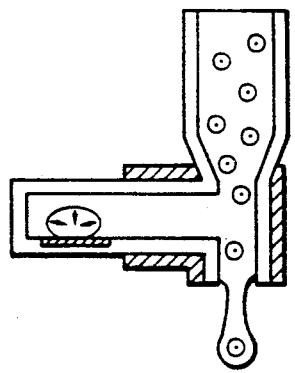
Figure 5D:
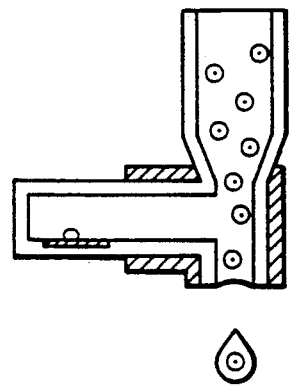

Another embodiment of the present invention will now be described. FIG. 4 shows the construction of another embodiment of the present invention. In FIG. 4, reference characters identical to those in FIG. 1 designate identical or equivalent members.

In the previous embodiment, a pressurizing mechanism is used to form a sheath flow and this sheath flow is discharged into the atmosphere to thereby make the cell-suspended liquid into droplets, whereas the present embodiment is characterized in that it does not use the sheath flow system, but the cell-suspended liquid is directly discharged as droplets from the nozzle unit 30 of FIG. 4.

FIG. 5 shows the detailed construction of the nozzle unit 30, and FIGS. 5A-5D show the manner in which droplets are discharged. In FIG. 5, the reference numeral 31 designates a nozzle having a rectangular cross-section of the order of 50 $\mu m \times 50$ $\mu m$ for containing therein cell-suspended liquid in which are suspended cells which are particles to be examined. The lower end of the nozzle 31 opens and forms an opening. A popular method of making this nozzle is a method of providing a minute groove on a substrate by etching or the photoresist process, and sticking a planar plate thereon, but this is not restrictive. The size of the cross-section of the nozzle is a size suitable for the size of particles to be examined. In the present embodiment, the object of measurement is considered to be blood, and since the size of various blood corpuscles contained in blood is of the order of 5 $\mu m$-30 $\mu m$, the size of the nozzle is set to 50 $\mu m \times 50$ $\mu m$, somewhat larger than the maximum size of blood corpuscles. The reference numeral 32 denotes a supply port for supplying therethrough the cell-suspended liquid sequentially into the nozzle 31. The references numeral 33 designates a heater provided in the nozzle, and the reference numeral 34 denotes a heat radiating member provided externally of the nozzle 31 for suppressing the temperature rise of the nozzle 31 caused by the heat conduction from the heater.

In this construction, the principle on which droplets are discharged is similar to that described in connection with FIG. 3, but the size of the opening and the capacity of the heater are set such that droplets discharged from the nozzle 31 have a diameter of the order of 50 $\mu m$-80 $\mu m$, and the dilution of the particle-suspended liquid is set such that a single cell particle is contained in the discharge droplet.

The cell-suspended liquid made into droplets in the manner described above is sorted in a manner similar to that described in connection with the embodiment shown in FIG. 1.

As regards the system for the discharge of droplets from the nozzles 18 and 30, as in the previous embodiment, droplets may be discharged by the use of an on-demand type droplet discharge nozzle using electrorestrictive vibrator such as a piezo-element (Reference Numeral 24 in FIG. 3A). FIGS. 7A and 7B illustrate the discharge of a liquid droplet using an electrorestrictive vibrator.

The present embodiment does not use a sheath flow and therefore eliminates the necessity of using a pressurizing mechanism and sheath liquid and thus, the apparatus becomes a simpler and more compact.

In the above-described embodiments, four discharge nozzles for fractionation are provided to effect five kinds of fractionations. However, the number of discharge nozzles is not limited thereto, but n+1 kinds of fractionations can be accomplished by n (n being 1 or greater integer) nozzles.

We claim:

1. An apparatus for fractionating particles in particle-suspended liquid in conformity with properties thereof, comprising:

measuring means for measuring the properties of individual particles in the particle-suspended liquid;

separating means for separating said particle-suspended liquid into separated droplets containing a plurality of the individual particles therein; and discharging means including a nozzle for selectively discharging a liquid droplet from said nozzle to collide with said separated droplets in accordance with a discharge signal generated on the basis of the result of said measurement by said measuring means.

2. An apparatus according to claim 1, wherein measuring means comprises optical measuring means for optically measuring the individual particles.

3. An apparatus according to claim 2, wherein said optical measuring means has:

a light source;

means for applying a light from said light source to the individual particles; and means for detecting the light from the particles to which the light is applied.

4. An apparatus according to claim 3, wherein said means for detecting the light has a sensor for detecting scattered light and/or fluorescence from the particles.

5. An apparatus according to claim 1, wherein said separating means forms the particle-suspended liquid into a fine stream and injects it into an atmosphere, and imparts vibration to it to thereby form it into droplets.

6. An apparatus according to claim 1, wherein said separating means discharges a slight amount of said particle-suspended liquid from a nozzle to thereby form it into droplets.

7. An apparatus according to claim 1, wherein said particles comprise cells.

8. An apparatus according to claim 1, further comprising accumulating means for discretely accumulating the particles fractionated in conformity with the properties thereof.

9. An apparatus according to claim 1, wherein said discharged droplet comprises physiological saline solution.

10. An apparatus according to claim 1, wherein said nozzle has a heating member, and said heating member is heated in accordance with said discharge signal to thereby create a bubble in the liquid in said nozzle and discharge droplets thereof.

11. An apparatus according to claim 1, wherein said nozzle has a vibration member and wherein said vibration member is vibrated in accordance with said discharge signal to thereby impart to the liquid in said nozzle and discharge droplets thereof.

12. An apparatus for fractionating particles in particle-suspended liquid in conformity with the properties thereof, comprising: means for causing individual particles in the particle-suspended liquid to flow to a position to be examined;

measuring means for measuring the properties of the individual particles flowing at the position to be examined;

separating means for separating said particle-suspended liquid into droplets containing the individual particles therein; and discharging means including a nozzle for selectively discharging a liquid droplet from said nozzle to collide with said separated droplets in accordance with a discharge signal generated on the basis of the result of said measurement by said measuring means.

13. An apparatus according to claim 12, further comprising accumulating means for discretely accumulating the particles fractionated in conformity with the properties thereof.

14. An apparatus according to claim 12, wherein said particles comprise cells.

15. A method of fractionating particles in a particle-suspended liquid in conformity with the properties thereof, comprising the steps of:

measuring the properties of individual particles in the particle-suspended liquid;

generating a discharge signal on the basis of a result from said measuring;

separating said particle-suspended liquid into droplets containing the individual particles therein; and selectively discharging a liquid droplet from a nozzle to collide with said separated droplets in accordance with the discharge signal generated on the basis of the result of said measuring.

16. An apparatus according to claim 15, wherein said particles comprise cells.

* * * * *

UNITED STATES PATENT AND TRADEMARK OFFICE
CERTIFICATE OF CORRECTION

PATENT NO. : 5,180,065

DATED : January 19, 1993

INVENTOR(S) : YOSHIYUKI TOUGE, ET AL.

It is certified that error appears in the above-identified patent and that said Letters Patent is hereby corrected as shown below:

COLUMN 1

Line 15, "the" should read --an--.
Line 23, "salin" should read --saline--.
Line 39, "measurement," should read --measurements,--.
Line 45, "and" should read --are--.

COLUMN 2

Line 19, "THE" should read --THE DRAWINGS--.
Line 30, "an" should read --an apparatus--.

COLUMN 3

Line 1, "18a 18d" should read --18a - 18d--.
Line 27, "created" should be deleted.
Line 41, "in shown" should read --in the initial state shown--.
Line 58, "[FIG. 3C].." should read --[FIG. 3C].--.

COLUMN 4

Line 25, "This" should read --That--.
Line 39, "will fall into" should read --the-- and "the" should read --will fall into--.
Line 43, "However" should read --However,--.
Line 57, "obtained" should read --is obtained--.

UNITED STATES PATENT AND TRADEMARK OFFICE
CERTIFICATE OF CORRECTION

PATENT NO.  : 5,180,065
DATED       : January 19, 1993
INVENTOR(S) : YOSHIYUKI TOUGE, ET AL.

It is certified that error appears in the above-identified patent and that said Letters Patent is hereby corrected as shown below:

COLUMN 6

Line 51, "impart" should read --impart impact--.
Line 56, "means" should read --¶ means--.

Signed and Sealed this

First Day of March, 1994

Attest:

BRUCE LEHMAN

Attesting Officer

Commissioner of Patents and Trademarks